US008834370B2

(12) United States Patent
Evert et al.

(10) Patent No.: US 8,834,370 B2
(45) Date of Patent: Sep. 16, 2014

(54) ULTRASONIC PERCUTANEOUS ENTERAL FEEDING TUBE (71) Applicant: Cook Medical Technologies LLC, Bloomington, IN (US)

(72) Inventors: Kathryn R. Evert, Bloomington, IN (US); Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/685,973

(22) Filed: Nov. 27, 2012

(65) Prior Publication Data
US 2013/0158401 A1 Jun. 20, 2013

Related U.S. Application Data (60) Provisional application No. 61/570,980, filed on Dec. 15, 2011.

(51) Int. Cl.
*A61B 8/00* (2006.01)
*A61J 15/00* (2006.01)
*A61B 8/08* (2006.01)
*A61M 39/00* (2006.01)
*A61M 39/02* (2006.01)
*A61B 19/00* (2006.01)

(52) U.S. Cl.
CPC ............ *A61B 8/48* (2013.01); *A61J 15/0038* (2013.01); *A61M 2039/0255* (2013.01); *A61M 2039/0261* (2013.01); *A61J 2015/0088* (2013.01); *A61B 8/0841* (2013.01); *A61J 15/0042* (2013.01); *A61J 15/0065* (2013.01); *A61M 39/00* (2013.01); *A61M 2039/0282* (2013.01); *A61B 2019/5425* (2013.01); *A61J 15/0015* (2013.01)

USPC ........... 600/439; 600/407; 600/409; 600/441; 600/437

(58) Field of Classification Search
USPC .......................... 600/409, 407, 437, 441, 439
See application file for complete search history.

(56) References Cited

U.S. PATENT DOCUMENTS 5,071,405 A 12/1991 Piontek et al.
5,073,166 A 12/1991 Parks et al.
(Continued)

OTHER PUBLICATIONS

Kimberly-Clark MIC Enteral Feeding Tubes and Accessories. [retrieved Jan. 13, 2011]. Retrieved from the Internet: <URL: http://www.kchealthcare.com/docs/U4850_MIC_Enteral_Tubes.pdf>.

(Continued)

*Primary Examiner* — Unsu Jung
*Assistant Examiner* — Joel Lamprecht
(74) *Attorney, Agent, or Firm* — Woodard, Emhardt, Moriarty, McNett & Henry LLP (57) ABSTRACT Among other things, a gastrostomy tube including a feeding tube that spans between an outer retention device and an inner retention device is disclosed. Embodiments of the inner retention device include an ultrasonic marker positioned within the inner retention device. The inner retention device and the ultrasonic marker have a variety of shapes or embodiments. The ultrasonic marker positioned in the inner retention device eliminates or reduces the use of fluoroscopy or endoscopy to position and later verify the location of the gastrostomy tube in a patient. Beneficially, the health risks associated with fluoroscopy and endoscopy are thereby eliminated or reduced with their associated disuse thereof. Moreover, the use of expensive hospital suites or operating rooms is eliminated or reduced with the use of portable ultrasound equipment that can be transported to a patient's bedside for verification of the location of the ultrasonic marker.

15 Claims, 5 Drawing Sheets

(56) References Cited

U.S. PATENT DOCUMENTS

| | | |
|---|---|---|
| 5,074,846 A | 12/1991 | Clegg et al. |
| 5,098,378 A | 3/1992 | Piontek et al. |
| 5,112,310 A | 5/1992 | Grobe |
| 5,167,627 A | 12/1992 | Clegg et al. |
| 5,391,159 A | 2/1995 | Hirsch et al. |
| 5,716,347 A | 2/1998 | Gibbs et al. |
| 5,720,734 A | 2/1998 | Copenhaver et al. |
| 5,865,816 A | 2/1999 | Quinn |
| 5,902,285 A | 5/1999 | Kudsk et al. |
| 6,045,536 A | 4/2000 | Meier et al. |
| 6,090,073 A | 7/2000 | Gill |
| 6,458,106 B1 | 10/2002 | Meier et al. |
| 6,471,676 B1 | 10/2002 | DeLegge et al. |
| 6,527,748 B1 | 3/2003 | Suzuki |
| 6,685,671 B1 | 2/2004 | Oishi et al. |
| 7,563,254 B2 | 7/2009 | DeLegge |
| 7,833,202 B2 | 11/2010 | Suzuki |
| 2010/0094116 A1* | 4/2010 | Silverstein .......... 600/409 |

OTHER PUBLICATIONS

Kimberly-Clark MIC PEG Feeding Tubes/Kits. [retrieved Jan. 13, 2011]. Retrieved from the Internet: <URL:http://www.kchealthcare.com/europe/ResourceCenter/Literature/DigestiveHealth/U6938_Z0416_SafetyPI.

Lynch, Christopher and Fang, John C., "Prevention and Management of Complications of Percutaneous Endoscopic Gastrostomy (PEG) Tubes", Practical Gastroenterology—Nutrition Issues in Gastroenterology, Series #22 (Nov. 2004), pp. 66, 68-70, and 72-76.

* cited by examiner

ULTRASONIC PERCUTANEOUS ENTERAL FEEDING TUBE

CROSS-REFERENCE TO RELATED APPLICATIONS

This application claims the benefit of U.S. Provisional Patent Application No. 61/570,980 filed Dec. 15, 2011, which is hereby incorporated by reference in its entirety.

BACKGROUND

The present disclosure relates generally to feeding tubes surgically implanted in patients who cannot receive their daily nutritional intake orally. More particularly, the disclosure relates to feeding tubes and techniques for their initial placement and subsequent location within the patient wherein ultrasound imaging is used.

When a patient is unable to swallow or cannot ingest food orally, enteral feeding is used to provide nutrition through a feeding tube that is inserted into the patient's digestive tract. Placement of the feeding tube in the patient's digestive tract may be temporary for the treatment of acute disabilities or permanent in the case of chronic disabilities. Percutaneous access for enteral nutrition may benefit placement of feeding tubes and allow patients to have a more active lifestyle and a more "normal" life. Presently, feeding tubes are designed for the delivery of enteral nutrition and/or medication into the stomach or the small bowel or intestine.

Several percutaneous gastrostomy methods are currently used which gain access to the stomach by a needle or cannula forced into the stomach. A percutaneous endoscopic gastrostomy ("PEG") is commonly performed by the "pull" technique, the "push" technique, or the introducer technique. There are many variations to the "pull" technique, the "push" technique, or the introducer technique as are commonly known. However, as described later, complications can occur which require the position of the implanted gastrostomy tube to be verified within the patient. Presently, either fluoroscopy or endoscopy is used to determine the position of the gastrostomy tube. Fluoroscopy exposes the patient to radiation emitted by the imaging system.

PEG tubes positioned in the body are typically held in place by both internal and external devices. For example, PEG tubes may have an internal retention mechanism such that the end of the PEG tube is held in place within the stomach or the intestine. This internal retention mechanism may take the form of a disk, dome, bowl, multiple flanges or leaves, a soft dome, or an inflatable balloon that is attached to the distal end of the feeding tube. The external retention mechanism is often affixed (e.g., adhesives, sutures) to the patient's skin or a mechanical device, such as a ring, is attached to the PEG tube exteriorly of the patient's skin but adjacent or next to the skin. Together these internal and external devices function to secure the PEG tube from inadvertent removal. Nonetheless, PEG tubes are often inadvertently dislodged or removed by patients or care-givers through excessive traction placed on connectors or tubing lines. When potential dislodgment of a PEG tube is suspected, the patient must undergo endoscopy or fluoroscopy to determine the position of the PEG tube. As described later, endoscopy and fluoroscopy can be accompanied with substantial risks to the patient.

Moreover, as the elderly population continues to grow, it is expected the use of PEG tubes will continue to rise. Some patients undergoing PEG tube placement are subject to complications associated with upper endoscopy and sedation. The most common complications of endoscopy include perforation of the stomach, small intestine, or colon, hemorrhage, and aspiration. Perforation of the body part can be verified using fluoroscopic imaging of the PEG tube in the patient. The use of fluoroscopic imaging exposes the patient to harmful radiation and requires the use of a radiology laboratory which is expensive.

Another complication that can arise with PEG tube placement is leakage of the tube feeding formula and/or gastric contents around the PEG site. One risk factor that can contribute to such a complication includes buried bumper (internal retention mechanism) syndrome. Buried bumper syndrome refers to the condition in which there is a partial or complete growth of gastric mucosa over the internal bumper or internal retention mechanism. The internal retention mechanism can migrate through the gastric wall and may lodge anywhere along the PEG tract. The buried bumper may be confirmed endoscopically or radiographically, again, exposing the patient to the risks associated with endoscopy and harmful radiation. Moreover endoscopy is performed in a hospital operating room or outpatient facility which are expensive.

Thus, there is a need for improvement in this field.

SUMMARY

This Summary is provided merely to introduce certain concepts and not to identify any key or essential features of the claimed subject matter.

In certain aspects, the present disclosure features embodiments of a gastrostomy tube assembly including an inner retention device, an outer retention device, and a feeding tube that spans between the inner retention device and the outer retention device. Beneficially, the inner retention device is viewable with ultrasound imaging thereby avoiding the use of fluoroscopy or endoscopy and the potential health risks associated therewith. In particular, the inner retention device includes an ultrasonic marker that is viewable with ultrasound imaging. Some shapes of the inner retention device include a bowl, disk, or an expandable component, to name a few. The ultrasonic marker includes a coil wire, flatwire, braided material, a plurality of shaped markers, or a plurality of dimples wherein each of the ultrasonic markers is positioned in the inner retention device. The ultrasonic marker is made of a material that is viewable with ultrasound imaging.

In other of its aspects, the present disclosure features a gastrostomy tube assembly including an inner retention device that includes an expandable component, an outer retention device, a feeding tube that spans between the inner retention device and the outer retention device, and an ultrasonic marker attached to the feeding tube wherein the ultrasonic marker is positioned within the expandable component and the ultrasonic marker is viewable with ultrasound imaging. In one particular embodiment, the ultrasonic marker is a tube shape. In this form, the ultrasonic marker being a tube shape is made of polymer, tungsten, and barium.

Beneficially, the initial placement of a gastrostomy tube in a patient can be positioned with ultrasound imaging wherein the inner retention device is viewable with ultrasound imaging to thereby place the feeding tube in the patient. After placement of the gastrostomy tube in the patient, the location of the inner retention device in the patient can be checked with ultrasound imaging instead of fluoroscopy.

Among other things, there is disclosed apparatus for a gastrostomy tube or gastrostomy tube assembly that includes an inner retention device, and outer retention device, and a feeding tube that spans between the inner retention device and the outer retention device, such feeding tube having a lumen with a central longitudinal axis. At least one ultrasound marker for visualization under ultrasound imaging is also provided, positioned at a lateral distance from said central longitudinal axis and extending around said central longitudinal axis. The marker is echogenic, referring generally to the ability to easily or clearly reflect ultrasound energy, or to the ability to be easily distinguished under ultrasound imaging from adjacent or other items, pieces or structures. In particular embodiments, the inner retention device includes a wall portion and the marker is within the wall portion. The marker(s) may comprise a plurality of dimples positioned in the wall which are at least partially defined by an echogenic material. Embodiments are also described having the wall defining a bowl shape that defines a rim, with the marker comprising a coil that extends at least part way around the rim. Such a coil may have windings around a winding axis, and the winding axis may curve around the central longitudinal axis of the feeding tube and be along the rim of the inner retention device. Alternatively, the wall can have a curved outer surface and a curved inner surface, with the coil being a spiral wire positioned in the wall between the curved outer and inner surfaces and with windings around a winding axis that is substantially parallel to that central longitudinal axis.

Also disclosed is a gastrostomy tube assembly that includes an inner retention device having an expandable component, an outer retention device, a feeding tube that spans between the inner retention device and the outer retention device, and an ultrasound marker attached to the feeding tube and positioned within the expandable component so that the marker is viewable under ultrasound imaging. Such markers may be a wire coil or otherwise made of metal, may be in a tube shape, or may be of one or more of a polymer, tungsten, and/or barium.

Methods disclosed include a method of determining the location of a gastrostomy tube in a patient, such as providing a gastrostomy tube that includes an inner retention device opposite an outer retention device and a feeding tube that spans between the inner retention device and the outer retention device, with the inner retention device being viewable using ultrasound, and using ultrasound imaging to determine the location of the inner retention device in the patient. The inner retention device can include an ultrasound or echogenic marker. For example, the inner retention device may have generally a bowl shape and the marker can be a spiral or other coil. Alternatively or additionally, the inner retention device can include a plurality of dimples that are viewable with ultrasound imaging, and can have a disc shape.

Further forms, objects, features, aspects, benefits, advantages, and embodiments of the present disclosure will become apparent from a detailed description and drawings provided herewith.

DESCRIPTION OF THE SELECTED EMBODIMENTS

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. One embodiment is shown in great detail, although it will be apparent to those skilled in the relevant art that some features that are not relevant to the present disclosure may not be shown for the sake of clarity.

As disclosed above, in certain aspects, the present disclosure provides unique products and methods for positioning a gastrostomy tube in a patient's digestive tract. Embodiments of gastrostomy tubes described herein include an inner retention device, an outer retention device, and a feeding tube that spans between the inner retention device and the outer retention device. In particular, an ultrasonic marker is positioned within the inner retention device to enable placement and location of the inner retention device and the gastrostomy tube via ultrasound or sonogram imaging.

Embodiments of the present disclosure are illustrated with reference to a gastrostomy tube; however, the embodiments may find equally advantageous application in other tube assemblies, such as a jejunostomy tube.

The terms "inner" and "outer," as used herein with respect to the gastrostomy tube of the disclosure, are to be understood to be used with reference to the orientation of the gastrostomy tube when placed in the patient, inner being in the direction of inside the body of the patient, and outer being in the direction of outside the body.

The inner retention device is configured to receive nutrition or other medical necessities via the feeding tube. The outer retention device is configured to receive the nutrition or medical necessities and pass those elements into the feeding tube. The inner retention device is also configured and positioned in the body to maintain the position of the feeding tube in the gastrostomy tract and stomach. The outer retention device is also configured and positioned exteriorly to the body to maintain the position of the feeding tube in the gastrostomy tract.

Embodiments of the present disclosure include one or more ultrasonic markers positioned within the inner retention device. The embodiments of the ultrasonic markers disclosed herein can be incorporated into a variety of inner retention devices; however, only a few example inner retention devices are described. The ultrasonic marker can be positioned in a configuration within the inner retention device that is beneficial to the placement of the feeding tube. The ultrasonic markers are highly visible with ultrasound imaging, and so fluoroscopic or other radiation are not required to view these ultrasonic markers to determine the position of the inner retention device and feeding tube within the patient's digestive tract while the gastrostomy tube is placed in the patient. Moreover, to verify or check the position of the feeding tube and/or the inner retention device at a time after the initial placement, ultrasound can again be used to locate the position of the ultrasonic markers, the feeding tube, and the inner retention device.

Additional benefits of these novel ultrasonic markers include the use of less expensive ultrasound equipment at a patient's bedside or doctor's office to locate or position a feeding tube within a patient as compared to radiation or endoscopy equipment in a hospital suite which can be more expensive. In the hospital or nursing home environment, ultrasound equipment is typically portable and can be transported to a patient's bed rather quickly; therefore, a medical suite or operating room is not necessary for use of such equipment. Additionally, with portable ultrasound equipment, the patient can remain resting comfortably in their bed instead of being transported and moved to a hospital suite or operating room. Eliminating or reducing the use of radiation equipment and medical suites or operating rooms to initially place and/or later check the location of the gastrostomy tube reduces the overall cost of the medical procedures associated with gastrostomy tubes. Another benefit of the ultrasound imaging is the elimination or reduction of exposure to radiation or fluoroscopy as typically required with traditional gastrostomy tubes.

Figure 1:
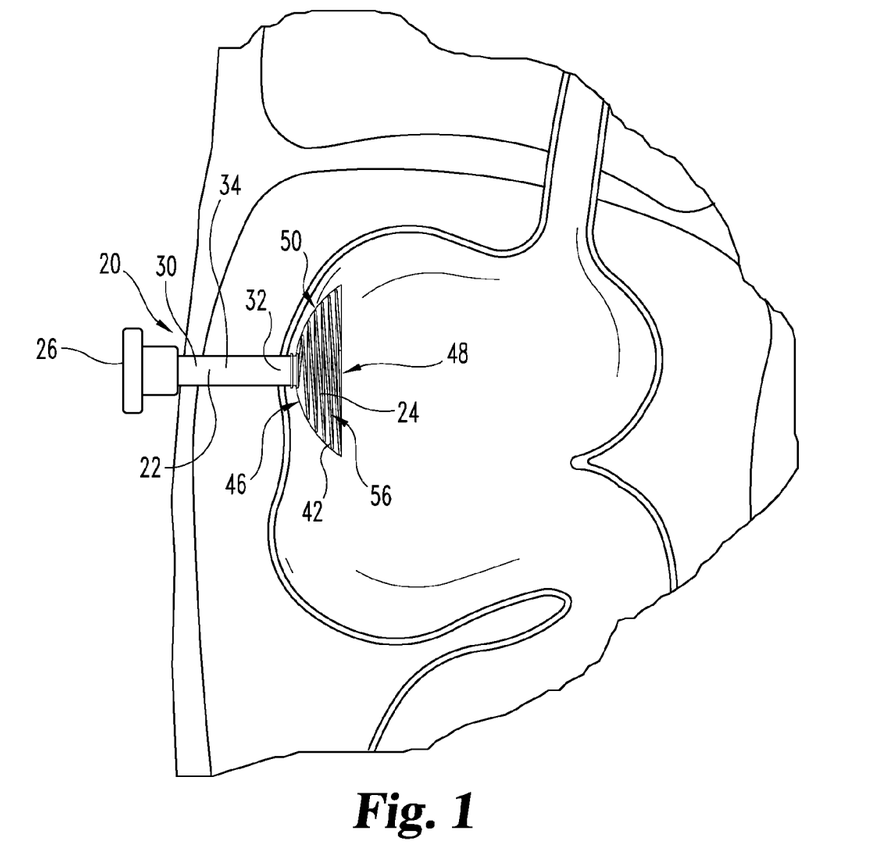
FIG. 1 is a cross-sectional view of one embodiment of a gastrostomy tube positioned in the stomach of a patient.
Figure 2:
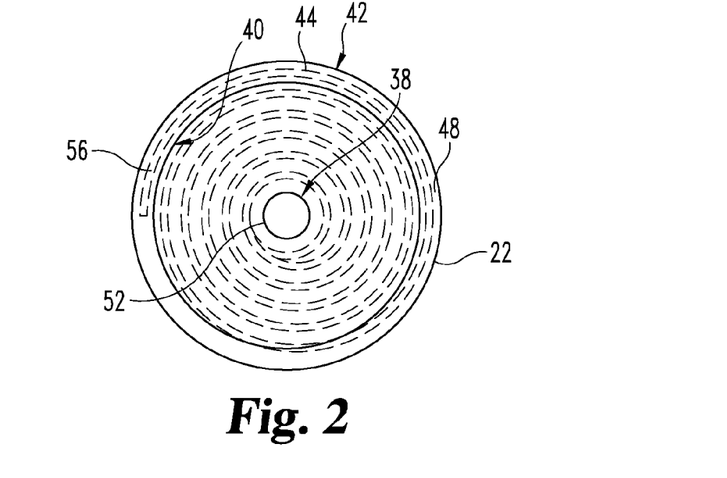
FIG. 2 is an end view of the FIG. 1 embodiment.

Referring now to the drawings, FIGS. 1 and 2 illustrate one embodiment of a gastrostomy tube 20. Gastrostomy tube 20 is shown positioned in the stomach of a patient and extends through a stoma created through the abdominal and gastric walls. Gastrostomy tube 20 includes a feeding tube 22 that spans between an inner retention device 24 and an outer retention device 26.

The feeding tube 22 includes a proximal end 30 opposite a discharge end 32 and a segment 34 spanning between the proximal end 30 and the discharge end 32. The feeding tube 22 includes a feeding lumen 38 that spans interiorly from the proximal end 30 to the discharge end 32. The length of the feeding tube 22 can be adjusted to accommodate the individual and medical condition. For example, the feeding tube 22 can be longer to extend through the outer retention device 26 such that the proximal end 30 is positioned beyond the outer retention device 26. As another example, the feeding tube 22 can be longer to extend through the inner retention device 24 such that the discharge end 32 extends beyond the inner retention device 24 and further into the stomach.

In one embodiment (not illustrated), the feeding tube 22 includes one or more ultrasonic feeding tube markers positioned along the length of the feeding tube 22 wherein the markers are visible with ultrasound imaging. The ultrasonic feeding tube markers are positioned, in particular embodiments, in standard or uniform increments along the length of the feeding tube 22. The first ultrasonic feeding tube marker may be positioned at the discharge end 32, and each subsequent marker is positioned on the feeding tube 22 at a designated increment.

The feeding tube 22 is formed of materials that are commonly used for feeding tubes. Some examplary materials include silicone, rubber, plastic, polymer, or other biocompatible materials.

Turning now to the inner retention device 24, the illustrated embodiment of inner retention device 24 has a bowl or semi-circular shape. It will be understood that other embodiments of inner retention device 24 are contemplated, such as those having a disc shape or cylindrical shape. Inner retention device 24 may also be formed as or part of a balloon or expandable device. The illustrated embodiment of inner retention device 24 has a curved inner surface 40, a curved outer surface 42, and a wall 44 between the inner surface 40 and the outer surface 42. The inner retention device 24 also includes a base 46, an outer rim 48, and a mid-section 50 that spans between the base 46 and the outer rim 48. The center of the base 46 defines an opening 52 that connect to and corresponds in size and shape to the feeding lumen 38. Moreover, the discharge end 32 of tube 22 connects with the opening 52 and the base 46 of the inner retention device 24 to attach the feeding tube 22 to the inner retention device 24 to enable nutrition or medicine to pass into the stomach. As seen in the example of FIG. 1, base 46 is positioned against the stomach wall and rim 48 is pointed toward the center of the stomach.

Inner retention device 24 is formed of materials that are commonly used for feeding tubes. As stated previously, some example materials include silicone, rubber, plastic, polymer, or other biocompatible materials. The inner retention device 24 may be made of the same material as the feeding tube 22 or the inner retention device 24 may be made of a different material than the feeding tube 22.

In one embodiment, the inner retention device 24 has a collapsed or folded state for insertion into a patient. After insertion into the patient, such an inner retention device 24 opens or extends, e.g. to an unstressed condition or to full size. The illustrated embodiment in FIGS. 1 and 2 shows the inner retention device 24 in an open or extended state. In another embodiment, the inner retention device 24 is flexible to bend or deflect during insertion into and removal from the patient. After insertion into the patient, the inner retention device 24 can assume a relaxed or unstressed position as illustrated in FIGS. 1 and 2.

The inner retention device 24 further includes an ultrasonic marker 56 positioned within the wall 44 such that the ultrasonic marker 56 does not extend through the inner surface 40 or the outer surface 42. The ultrasonic marker 56 is visible using ultrasound imaging, thus eliminating the requirement of fluoroscopy or radiation to determine the location of the inner retention device 24 within a patient. The illustrated embodiment of ultrasonic marker 56 is a spiral wire positioned in the wall 44 extending around retention device 24 from the outer rim 48 to the base 46. In that embodiment, windings or coils of wire wind around the longitudinal axis of tube 22 and successive windings or coils have larger diameters as the coils extend away from tube 22, so as to be maintained within wall 44. For example, an axis around which the wire winds may be parallel to or coincident with the central longitudinal axis of tube 22.

As will be appreciated, a larger area or portion of the inner retention device 24 through which ultrasonic marker 56 wraps or extends generates greater or more distinct visibility by ultrasound. Ultrasonic marker 56 is flexible in this embodiment during placement or delivery into the patient, and maintains flexibility while the inner retention device 24 is positioned in the patient. A flexible ultrasonic marker 56 is more comfortable for the patient during placement and final positioning and while implanted in the patient. Other embodiments of ultrasonic marker 56 include a normal, flatwire or stretched coil, or may be or include a laser cut coil, dimpled coil, expanded stent, marker band, modified marker band, or a braided material. Ultrasonic marker 56 can be or include a plurality of shaped markers, for example of one or more of spherical, rounded, square, triangular, or polygonal shape. Ultrasonic marker 56 is made of material that reflects a different wavelength than does the material used for the inner retention device 24 or feeding tube 22 under ultrasonic imaging. Beneficially, the variance in wavelength between the material of the ultrasonic marker 56 and the inner retention device 24 enables the ultrasound equipment to better distinguish or otherwise view marker 56, and thus observe the placement and/or orientation of retention device 24 and tube 22. As examples, ultrasonic marker 56 can be made of stainless steel, platinum, silver, tungsten, barium, or another metal, plastic, fiber, air pocket, a combination of any of these materials, or other materials that are biocompatible and viewable by ultrasound imaging.

The outer retention device 26 in one embodiment is provided as illustrated in FIG. 1. The configuration of the outer retention device 26 is not critical and those skilled in the art will appreciate that various designs are operable in the present disclosure.

Figure 3:
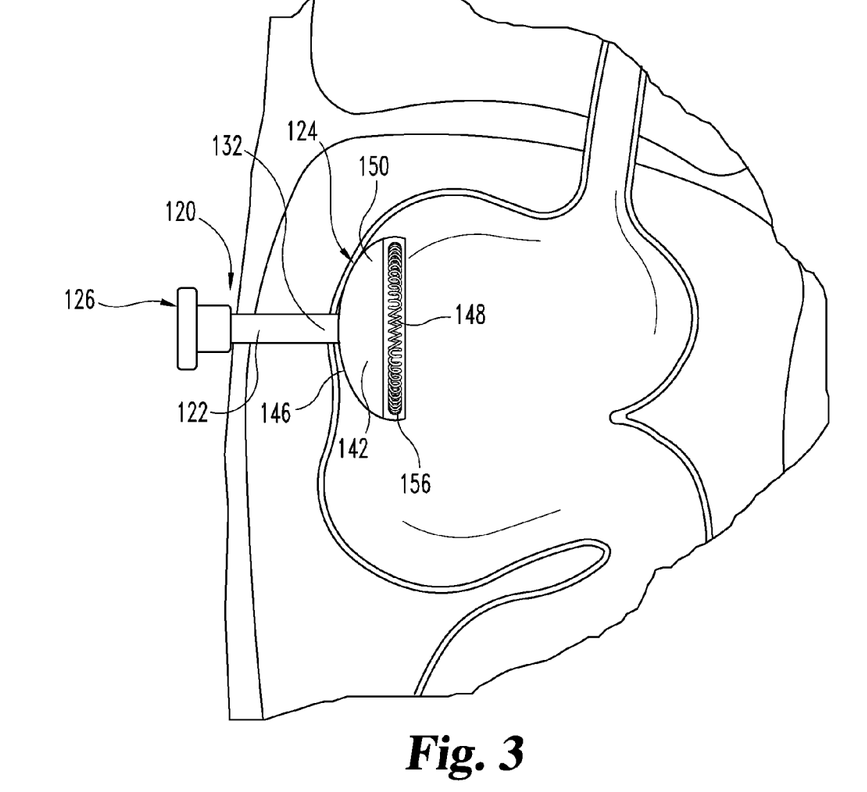
FIG. 3 is a cross-sectional view of a second embodiment of a gastrostomy tube positioned in the stomach of a patient.
Figure 4:
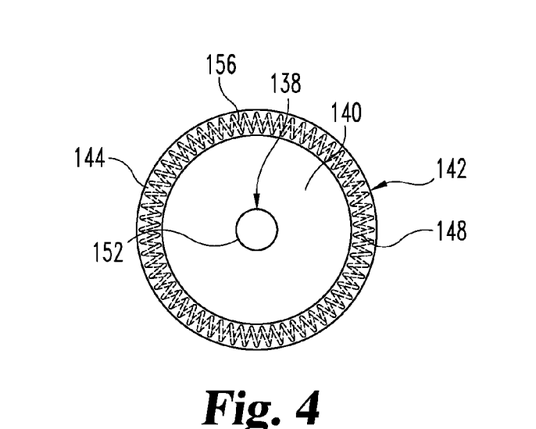
FIG. 4 is an end view of the FIG. 3 embodiment.

Turning now to FIGS. 3 and 4, another embodiment of a gastrostomy tube 120 is illustrated. Gastrostomy tube 120 includes a feeding tube 122 that spans between an inner retention device 124 and an outer retention device 126. Inner retention device 124, feeding tube 122 and outer retention device 126 are similar to inner retention device 24, feeding tube 22, and outer retention device 26, respectively; therefore, for the sake of brevity similar features will not be discussed.

The inner retention device 124 has a bowl or semicircular shape in the embodiment of FIG. 3; however, inner retention device 124 may be configured differently in other embodiments. Some example shapes for inner retention device 124 include a disc or cylindrical shape. The inner retention device 124 has an inner surface 140 and an outer surface 142 and a wall 144 between the inner and the outer surfaces 140 and 142. The inner retention device 124 also includes a base 146, a rim 148, and a mid-section 150 that spans between the base 146 and the rim 148. The base 146 is shown in the FIG. 3 example as positioned against the stomach wall with rim 148 pointed generally into or toward the center of the stomach. The base 146 defines an opening 152 that connects to and corresponds in size and shape to the feeding lumen 138 of feeding tube 122. Moreover, the discharge end 132 of tube 122 connects with the opening 152 and the base 146 of the inner retention device 124 to attach the feeding tube 122 to the inner retention device 124 such that nutrition or medicine passes through the feeding lumen 138 and the opening 152 and discharges into the stomach. The inner retention device 124 also includes an ultrasonic marker 156 positioned within or closely adjacent rim 148 such that the ultrasonic marker 156 does not extend through rim 148. As such, rim 148 has a width, thickness, and length to accommodate the ultrasonic marker 156.

As illustrated, the embodiment of ultrasonic marker 156 is a coiled wire positioned in rim 148 and extending along the length of some or all of rim 148. The coils or windings of wire in marker 156 wind around a central axis that is curved or circular to substantially match the planar shape of rim 148. For example, that curved central axis lies in a plane and is substantially parallel to opening 152 in the illustrated embodiment, and the center of that curve of the curved central axis is within the area surrounded by rim 148 (e.g. along the central longitudinal axis of tube 122). Further, the illustrated embodiment of marker 156 is positioned within retention device 124 as far from opening 152 as possible. It will be understood that such curved coils may be placed at other positions between rim 148 and opening 152. Some embodiments of ultrasonic marker 156 include a normal, flatwire, or stretched coil shape, and/or a laser cut coil, dimpled coil, expanded stent, marker band, modified marker band, or a braided material. An additional embodiment of ultrasonic marker 156 can include a plurality of shaped markers that are positioned in the rim 148. For example, the ultrasonic marker 156 can have a sphere, square, triangle, polygonal, or other shape. The ultrasonic marker 156 is made of similar material as ultrasonic marker 56 and is visible using ultrasound imaging.

Figure 5:
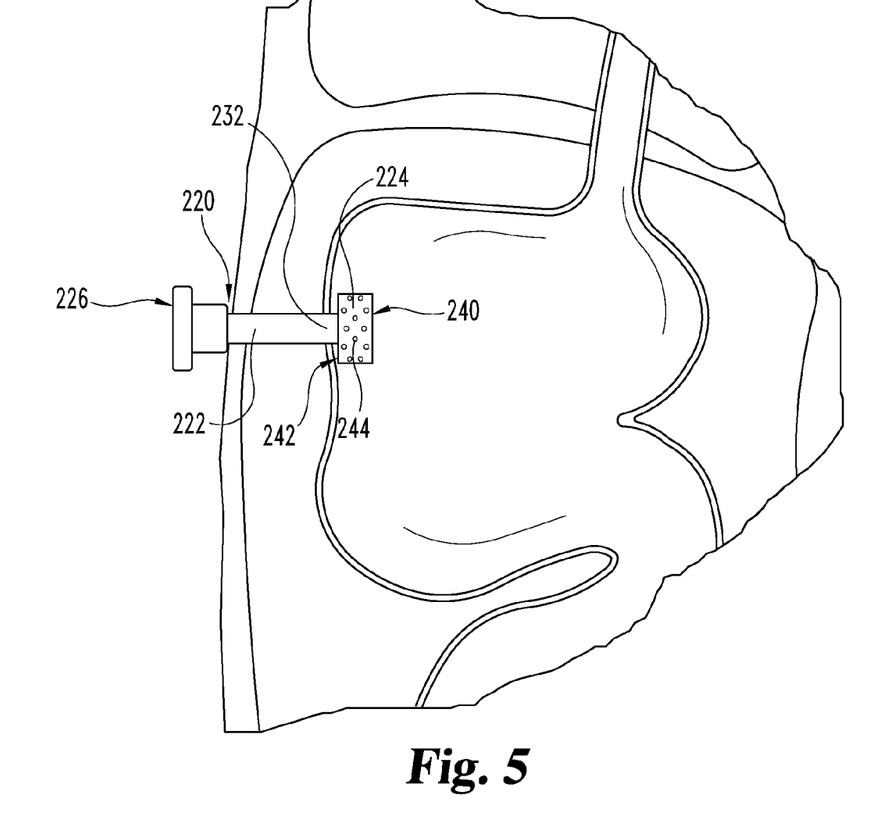
FIG. 5 is a cross-sectional view of a third embodiment of a gastrostomy tube positioned in the stomach of a patient.
Figure 6:
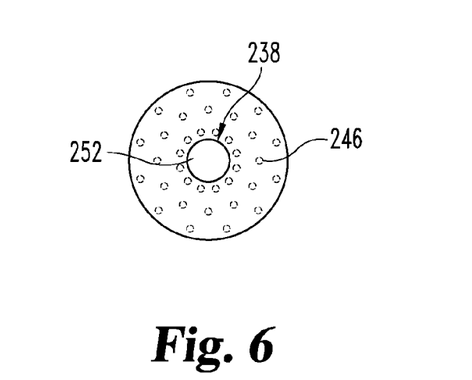
FIG. 6 is an end view of the FIG. 5 embodiment.

Turning now to FIGS. 5 and 6, another embodiment of a gastrostomy tube 220 is illustrated. Gastrostomy tube 220 includes a feeding tube 222 that spans between an inner retention device 224 and an outer retention device 226. Feeding tube 222 and outer retention device 226 are similar to feeding tube 22 and outer retention device 26, respectively; therefore, for the sake of brevity similar features will not be discussed.

The inner retention device 224 is a disk shape. However, in other embodiments the inner retention device 224 may be shaped differently such as a bowl, expandable component, or other shape. The inner retention device 224 has an inner surface 240, an outer surface 242, and a wall 244 that spans between the inner surface 240 and the outer surface 242. The inner retention device 224 defines an opening 252 in the wall 244 that spans between the inner and outer surfaces 240 and 242, respectively. The opening 252 connects to and is sized to meet feeding lumen 238 of feeding tube 222. Moreover, the discharge end 232 connects with the opening 252 and wall 244 of the inner retention device 224 to attach the feeding tube 222 to the inner retention device 224 such that nutrition or medicine passes through the feeding lumen 238 and the opening 252 and discharges into the stomach.

In this embodiment, the ultrasonic marker includes a plurality of dimples or nodules 246 positioned in the wall 244. As illustrated in FIGS. 5 and 6, the plurality of dimples 246 are round or spherical, however, in other embodiments the plurality of dimples 246 have a different shape. Some example shapes include square, pyramidal, or another polygonal or curved shape. Additional ultrasonic markers as described in the present disclosure can be incorporated into the inner retention device 224 along with the plurality of dimples 246.

The plurality of dimples 246 can be positioned or formed within the wall 244. For example, hollowed pieces of or coated by an echogenic material and/or one that is different than that used for inner retention device 224 may be implanted, pressed into, or otherwise placed into wall 244 with their respective hollows or concave surfaces exposed or outwardly directed. The plurality of dimples 246 can be made of or coated with echogenic materials such as stainless steel, tungsten, barium, or another metal, plastic, fiber, a combination of any of these materials, or other materials that are biocompatible and viewable by ultrasound imaging when positioned in a patient.

Figure 7:
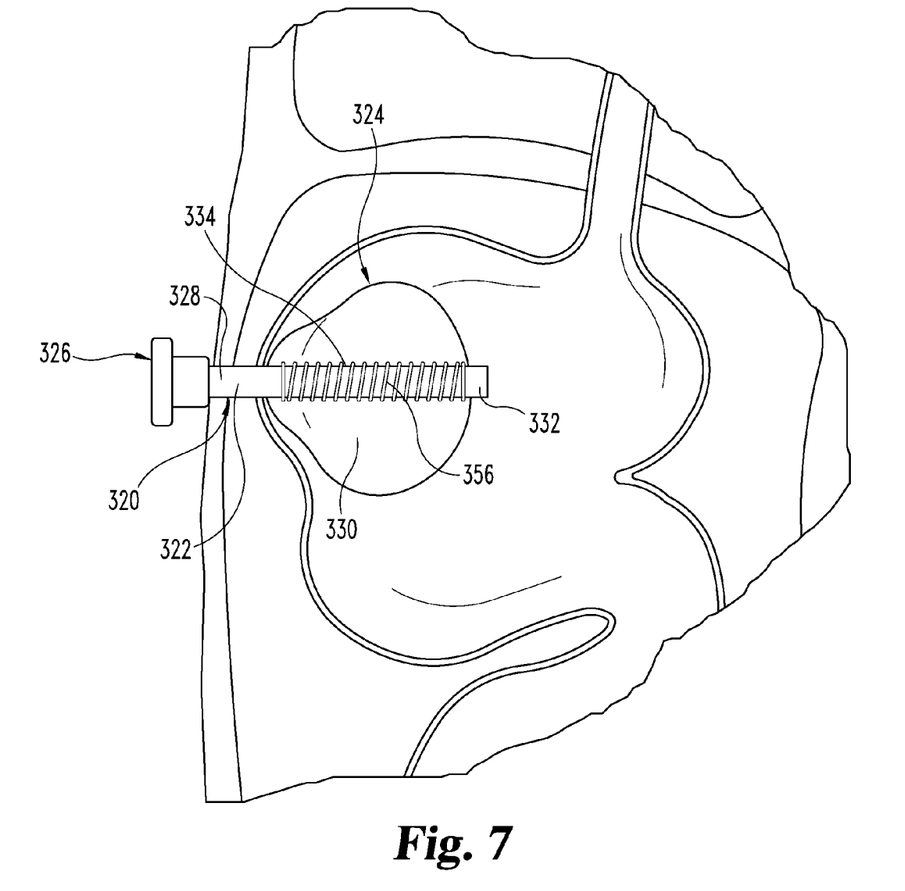
FIG. 7 is a cross-sectional view of a fourth embodiment of a gastrostomy tube positioned in the stomach of a patient.

Turning now to FIG. 7, another embodiment of a gastrostomy tube 320 is illustrated. Gastrostomy tube 320 includes a feeding tube 322 that spans between an inner retention device 324 and an outer retention device 326. Feeding tube 322 includes a proximal end 328 opposite a discharge end 332 and a segment 334 spanning between the proximal end 328 and the discharge end 332. Feeding tube 322 and outer retention device 326 are similar to feeding tube 22 and outer retention device 26, respectively; therefore, for the sake of brevity similar features will not be discussed.

Inner retention device 324 includes an expandable component 330 typically referred to as a balloon. Expandable component 330 is made of silicone or other expandable material that is also biocompatible. In one form, the expandable component 330 is configured to be inserted into the patient in a fully inflated state wherein there is no inflation/deflation valve or lumen connected to the expandable component 330. In another form, the expandable component 330 includes an inflation/deflation valve or lumen and is configured to be inserted in a deflated state into the patient. After the expandable component 330 is positioned in the patient, the expandable component 330 is inflated. To remove the expandable component 330, the expandable component 330 is deflated.

Inner retention device 324 also includes an ultrasonic marker 356. As illustrated, the ultrasonic marker 356 is a coil wire positioned under the expandable component 330 and which spans along the feeding tube 322. As such, the ultrasonic marker 356 is positioned on and/or around the feeding tube 322. In particular, the ultrasonic marker 356 can span the length of the expandable component 330 or can extend along the feeding tube 322 a shorter distance than the length of expandable component 330. In any of these configurations, expansion of the expandable component 330 will not affect or move the ultrasonic marker 356. Moreover, similar to ultrasonic marker 56, ultrasonic marker 356 is visible using ultrasound imaging.

Some embodiments of ultrasonic marker 356 include a normal, flatwire, or stretched coil shape. Yet other embodiments of ultrasonic marker 356 include a laser cut coil, dimpled coil, expandable stent, marker band, modified marker band, or a braided material. An additional embodiment of ultrasonic marker 356 can include a plurality of shaped markers positioned along the feeding tube 322 and under the expandable component 330. For example, ultrasonic marker 356 can be made up of spherical, rounded, square, triangular, or polygonal shape pieces. Similar to marker 56, the ultrasonic marker 356 is made of stainless steel, platinum, tungsten, barium, or another metal, plastic, fiber, a combination of any of these materials, or any other material that is also biocompatible and viewable by ultrasound imaging.

Inner retention device 324 is secured to the feeding tube 320 by various techniques. Some techniques to attach the inner retention device 324 to the feeding tube 320 include adhesive, glue, mechanical fasteners, or other means.

Figure 8:
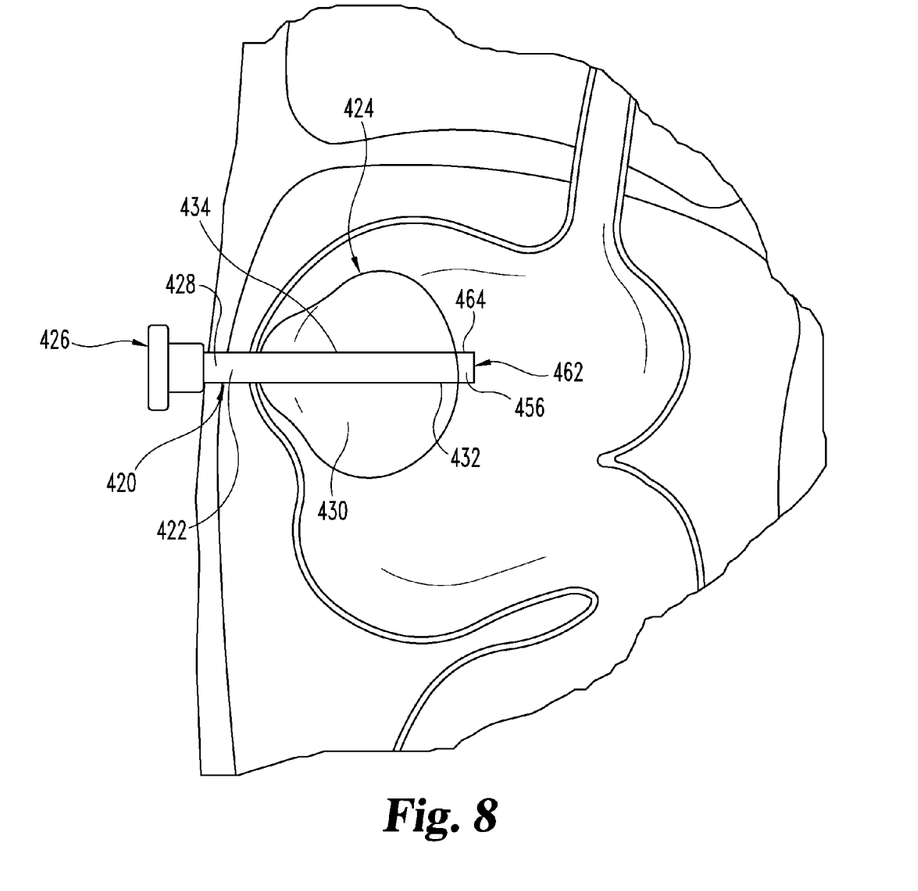
FIG. 8 is a cross-sectional view of a fifth embodiment of a gastrostomy tube positioned in the stomach of a patient.

In yet another embodiment illustrated in FIG. 8 is a gastrostomy tube 420. Gastrostomy tube 420 includes a feeding tube 422 that spans between an inner retention device 424 and an outer retention device 426. Feeding tube 422 includes a proximal end 428 opposite a discharge end 432 and a segment 434 that spans between the proximal end 428 and the discharge end 432. Feeding tube 422 and outer retention device 426 are similar to feeding tube 22 and outer retention device 26, respectively; therefore, for the sake of brevity similar features will not be discussed.

Inner retention device 424 includes an expandable component 430 that is similar to expandable component 330; therefore, for the sake of brevity similar features will not be discussed.

In this embodiment, the ultrasonic marker 456 is positioned at the discharge end 432 of the feeding tube 422. The ultrasonic marker 456 is configured to approximate or match the cross-sectional shape of the discharge end 432 and the lumen of the feeding tube 422. As such, the ultrasonic marker 456 is a tube shape defining an opening 462 and a wall 464 that extends around the opening 462. The opening 462 of the ultrasonic marker 456 is about the same size as the lumen of the feeding tube 422. As such, nutrition and medicine passes through the lumen of the feeding tube 422 and the opening 462 of the ultrasonic marker 456.

In this particular embodiment, the ultrasonic marker 456 is made of a mixture of polymer, tungsten, and barium to form a loaded tip that is attached to or formed with the feeding tube 422. However, in other embodiments, ultrasonic marker 456 is made from other materials such as stainless steel, platinum, or another metal, plastic, fiber, a combination of any of these materials, or another material that is biocompatible and viewable by ultrasound imaging. The ultrasonic marker 456 is then attached to the discharge end 432 of the feeding tube 422 by various techniques. Some techniques include glue, adhesive, mechanical fasteners, or other means. As can be appreciated, the means used to attach ultrasonic marker 456 to feeding tube 422 are biologically compatible.

One technique that can be used to position the gastrostomy tube 20 within a patient's digestive tract includes positioning the feeding tube 22 in a patient's stomach such that the feeding tube 22 and the inner retention device 24 are advanced through the patient's skin near their stomach and into their stomach. Gastrostomy tube 120, gastrostomy tube 220, gastrostomy tube 320, and gastrostomy tube 420 can be placed similarly as gastrostomy tube 20. In this technique, a needle puncture is made through the skin near the stomach and a wire guide (not shown) is advanced through the opening in the skin and into the stomach. Next, the openings through the skin and stomach are dilated or distended by a dilator (not shown) that is passed over the wire guide to create a dilated tract or an open stoma. The dilator is then removed.

Tube 20, with inner retention device 24 in a collapsed state and feeding tube 22, is then placed over the wire guide, through the dilated tract and the opening in the stomach to a final position inside the stomach under ultrasound visualization. Ultrasound marker 56 is viewable using ultrasound such that the physician can position the inner retention device 24 and feeding tube 22 inside the stomach without endoscopy or fluoroscopy. The wire guide is then removed from the patient. The collapsed inner retention device 24 opens after its exit from the dilator or other introducer, and feeding tube 22 extends out of the opening in the stomach. The ultrasound marker 56 is viewable by ultrasound as the inner retention device 24 in an expanded state within the stomach is pulled by the medical practitioner towards the opening in the skin. As the inner retention device 24 is pulled toward the opening in the skin, the stomach wall adjacent the inner retention device 24 is also pulled close to the abdomen. The outer retention device 26 is positioned over the stoma and maintains the position of the feeding tube 22 within the opening. An additional length of feeding tube 22 can extend outside the patient's body and beyond the outer retention device 26. This additional length of feeding tube 22 can be attached to the skin of the abdomen. Nutrition or medications are then supplied through the gastrostomy tube 20 and directly into the stomach.

Another technique that can be used to position the gastrostomy tube 20 within a patient's digestive tract includes positioning the feeding tube 22 in a patient's stomach wherein the feeding tube 22 is first advanced through the patient's mouth, down the esophagus, into their stomach, and out through an opening created in the patient's skin near the stomach. To perform this procedure, a medical practitioner typically makes a needle puncture through the skin near the stomach and a wire guide (not shown) is advanced through the opening in the skin and into the stomach. Next, the openings through the skin and stomach are dilated or distended by a dilator (not shown) that is passed over the wire guide to create a dilated tract or an open stoma. The dilator is then removed. A surgical snare or other medical device that can grasp or hold the wire guide is then guided through the mouth, the esophagus, and into the stomach where the wire guide is positioned. Using the surgical snare, the medical practitioner then takes hold of the wire guide in the stomach. The feeding tube 22 with the inner retention device 24 in a collapsed position is pulled along with the snare down through the mouth, through the esophagus, through the stomach and out the opening that was created through the stomach and skin. If not completely collapsed, the inner retention device 24 will flexibly deform as it is pulled through the body. The inner retention device 24 in a collapsed position will open after being positioned in the stomach to form a bowl-like configuration (e.g. FIG. 1). The feeding tube 22 is now positioned in the stomach with the tube portion sticking out of the opening. The outer retention device 24 is attached to the feeding tube 22 and the outer retention device 24 is positioned over the stoma. Together the inner retention device 24 and the outer retention device 24 maintain the position of the feeding tube 22 within the opening. Nutrition or medications are then supplied through the gastrostomy tube 20 and directly into the stomach.

In embodiments of gastrostomy tubes (e.g. 320, 420) having expandable components, it will be understood that the insertion and positioning can be performed substantially as discussed above. With tubes 320, 420 positioned so that expandable components 330, 430 are within the stomach and feeding tubes 322, 422 extending through the stoma, components 330, 430 are inflated or otherwise expanded. Subsequently, pulling tubes 320, 420 through the stoma forces the stomach wall toward the skin, as indicated previously.

While the disclosure has been illustrated and described in detail in the drawings and foregoing description, the same is to be considered as illustrative and not restrictive in character, it being understood that only the preferred embodiment has been shown and described and that all changes, equivalents, and modifications that come within the spirit of the following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A gastrostomy tube assembly, comprising:
   an inner retention device configured for placement in a body of a patient, wherein the inner retention device is sized to maintain its position within the body of the patient;
   an outer retention device configured for placement exteriorly of the body of the patient, wherein the outer retention device is sized to maintain its position exteriorly the body of the patient;
   a feeding tube that spans between the inner retention device and the outer retention device, said feeding tube having a lumen with a central longitudinal axis, wherein the inner retention device and the outer retention device maintain the position of the feeding tube in a gastrostomy tract of the body of the patient, and
   at least one ultrasound marker for visualization under ultrasound imaging, said at least one marker positioned at a lateral distance from said central longitudinal axis and extending around said central longitudinal axis, said at least one ultrasound marker positioned in said inner retention device.

2. The assembly of claim 1, wherein said inner retention device includes a wall portion and said marker is placed within said wall portion.

3. The assembly of claim 2, wherein said at least one marker comprises a plurality of dimples positioned in said wall of said inner retention device, said plurality of dimples at least partially defined by an echogenic material.

4. The assembly of claim 2, wherein said wall of said inner retention device defines a bowl shape that defines a rim, and wherein said marker comprises a coil that extends at least part way around said rim.

5. The assembly of claim 4, wherein said coil has windings around a winding axis, said winding axis curving around said central longitudinal axis and being along said rim.

6. The assembly of claim 4, wherein said wall has a curved outer surface and a curved inner surface, and said coil is a spiral wire positioned in the wall between the curved outer and inner surfaces, said coil having windings around a winding axis, said winding axis being substantially parallel to said central longitudinal axis.

7. A gastrostomy tube assembly, comprising:
   an inner retention device that includes an expandable component configured for placement in a body of a patient, wherein the inner retention device is sized to maintain its position within the body of the patient;
   an outer retention device configured for placement exteriorly of the body of the patient, wherein the outer retention device is sized to maintain its position exteriorly the body of the patient;
   a feeding tube that spans between the inner retention device and the outer retention device, wherein the inner retention device and the outer retention device maintain the position of the feeding tube in a gastrostomy tract of the body of the patient; and
   an ultrasound marker attached to the feeding tube wherein the ultrasonic marker is positioned within the expandable component and the ultrasonic marker is viewable under ultrasound imaging.

8. The assembly of claim 7, wherein the marker is a wire coil.

9. The assembly of claim 8, wherein the marker is made of metal.

10. The assembly of claim 7, wherein the marker is a tube shape.

11. The assembly of claim 10, wherein the marker is made of polymer, tungsten, and barium.

12. A method of determining the location of a gastrostomy tube in a patient, comprising:
   providing a gastrostomy tube, the gastrostomy tube including an inner retention device opposite an outer retention device and a feeding tube that spans between the inner retention device and the outer retention device, wherein the inner retention device and the outer retention device maintain the position of the feeding tube in a gastrostomy tract of the body of the patient, wherein the inner retention device includes an ultrasonic marker that is viewable using ultrasound; and
   using ultrasound imaging to determine the location of the inner retention device in the patient.

13. The method of claim 12, wherein the inner retention device has a bowl shape and the ultrasound marker is a spiral coil.

14. The method of claim 12, wherein the inner retention device includes a plurality of dimples positioned therein, the plurality of dimples being viewable with ultrasound imaging.

15. The method of claim 14, wherein the inner retention device has a disc shape.

* * * * *